(12) United States Patent
Sato (10) Patent No.: US 10,174,084 B2
(45) Date of Patent: Jan. 8, 2019

(54) FUSION POLYPEPTIDES AND VACCINES

(71) Applicant: CEVA SANTE ANIMALE, Libourne (FR)

(72) Inventor: Takanori Sato, Kanagawa (JP)

(73) Assignee: CEVA SANTE ANIMALE, Libourne (FR)

( * ) Notice: Subject to any disclaimer, the term of this patent is extended or adjusted under 35 U.S.C. 154(b) by 0 days.

(21) Appl. No.: 14/783,117

(22) PCT Filed: Apr. 10, 2014

(86) PCT No.: PCT/EP2014/057287
§ 371 (c)(1),
(2) Date: Oct. 8, 2015

(87) PCT Pub. No.: WO2014/167060
PCT Pub. Date: Oct. 16, 2014

(65) Prior Publication Data
US 2016/0046676 A1 Feb. 18, 2016

(30) Foreign Application Priority Data
Apr. 11, 2013 (EP) .................................... 13163299

(51) Int. Cl.
| | |
|---|---|
| *C12N 15/86* | (2006.01) |
| *C07K 14/005* | (2006.01) |
| *A61K 39/12* | (2006.01) |
| *A61K 39/385* | (2006.01) |
| *C12N 7/00* | (2006.01) |
| *A61K 35/76* | (2015.01) |
| *A61K 39/00* | (2006.01) |

(52) U.S. Cl.
CPC ............ *C07K 14/005* (2013.01); *A61K 39/12* (2013.01); *A61K 39/385* (2013.01); *C12N 7/00* (2013.01); *A61K 39/00* (2013.01); *A61K 2039/552* (2013.01); *A61K 2039/6075* (2013.01); *C07K 2319/02* (2013.01); *C12N 2710/24021* (2013.01); *C12N 2710/24043* (2013.01); *C12N 2710/24122* (2013.01); *C12N 2750/10022* (2013.01); *C12N 2750/10034* (2013.01); *C12N 2750/10071* (2013.01)

(58) Field of Classification Search
CPC .............. A61K 2039/507; A61K 39/12; A61K 39/285; A61K 2039/5256; C07K 16/081; C07K 2319/02; C07K 14/005; C07K 2319/00; C12N 2710/24043; C12N 15/86; C12N 2710/24122; C12N 2830/00; C12N 2830/15; C12N 2710/24111
See application file for complete search history.

(56) References Cited

U.S. PATENT DOCUMENTS

2010/0150959 A1* 6/2010 Sheppard ............... A61K 39/12
424/204.1

FOREIGN PATENT DOCUMENTS

| EP | 2 564 869 | 3/2013 |
| WO | WO 2010/068969 | 6/2010 |

OTHER PUBLICATIONS

Isaacs et al. J. Virol. 1992, vol. 66, No. 12, pp. 7217-7224.*
Kwak et al. Virology 2004, vol. 322, pp. 337-348.*
Nawagitgul et al. J. Gene. Virol. 2000, vol. 81, pp. 2281-2287.*
Kwak, H. et al. "Improved protection conferred by vaccination with a recombinant vaccinia virus that incorporates a foreign antigen into the extracellular enveloped virion" *Virology*, May 1, 2004, pp. 337-348, vol. 322.
Katz, E. et al. "The Cytoplasmic and Transmembrane Domains of the Vaccinia Virus B5R Protein Target a Chimeric Human Immunodeficiency Virus Type 1 Glycoprotein to the Outer Envelope of Nascent Vaccinia Virions" *Journal of Virology*, Apr. 1997, pp. 3178-3187, vol. 71, No. 4.
Katz, E. et al. "Immunogenicity of Recombinant Vaccinia Viruses that Display the HIV Type 1 Envelope Glycoprotein on the Surface of Infectious Virions" *AIDS Research and Human Retroviruses*, Nov. 20, 1997, pp. 1497-1500, vol. 13, No. 17.
Ward, B. et al. "Visualization of Intracellular Movement of Vaccinia Virus Virions Containing a Green Fluorescent Protein—B5R Membrane Protein Chimera" *Journal of Virology*, May 1, 2001, pp. 4802-4813, vol. 75, No. 10.
Lin, H. et al. "Construction and immunogenicity of recombinant swinepox virus expressing capsid protein of PCV2" *Vaccine*, Sep. 1, 2012, pp. 6307-6313, vol. 30, No. 44.
Written Opinion in International Application No. PCT/EP2014/057287, dated Aug. 6, 2014, pp. 1-6.

* cited by examiner

*Primary Examiner* — Bao Q Li
(74) *Attorney, Agent, or Firm* — Saliwanchik, Lloyd & Eisenschenk (57) ABSTRACT

The present invention relates to novel immunogenic polypeptides and their use in vaccine compositions. The invention also relates to nucleic acids, vectors and cells which express the polypeptides and the uses thereof. The polypeptides of the invention more specifically comprise an immunogenic domain and a cell membrane addressing domain which is derived from a B5R gene. The invention is particularly suited to produce vaccines for non-human animals, particularly for vaccinating swine against PCV2 infection.

14 Claims, 4 Drawing Sheets
Specification includes a Sequence Listing.

SEQUENCE LISTING

```
<160> NUMBER OF SEQ ID NOS: 18

<210> SEQ ID NO 1
<211> LENGTH: 22
<212> TYPE: PRT
<213> ORGANISM: Artificial Sequence
<220> FEATURE:
<223> OTHER INFORMATION: Vaccinia Virus BR5-derived signal sequence

<400> SEQUENCE: 1

Lys Thr Ile Ser Val Val Thr Leu Leu Cys Val Leu Pro Ala Val Val
1               5                   10                  15

Tyr Ser Thr Cys Thr Val
            20

<210> SEQ ID NO 2
<211> LENGTH: 36
<212> TYPE: PRT
<213> ORGANISM: Artificial Sequence
<220> FEATURE:
<223> OTHER INFORMATION: Vaccinia Virus BR5-derived signal sequence

<400> SEQUENCE: 2

Lys Thr Ile Ser Val Val Thr Leu Leu Cys Val Leu Pro Ala Val Val
1               5                   10                  15

Tyr Ser Thr Cys Thr Val Pro Thr Met Asn Asn Ala Lys Leu Thr Ser
            20                  25                  30

Thr Glu Thr Ser
        35

<210> SEQ ID NO 3
<211> LENGTH: 191
<212> TYPE: PRT
<213> ORGANISM: Artificial Sequence
<220> FEATURE:
<223> OTHER INFORMATION: PCV2 ORF2

<400> SEQUENCE: 3

Gly Val Leu Asn Thr Arg Leu Ser Arg Thr Phe Gly Tyr Thr Ile Lys
1               5                   10                  15

Arg Thr Thr Val Lys Thr Pro Ser Trp Ala Val Asp Met Met Arg Phe
            20                  25                  30

Asn Ile Asn Asp Phe Val Pro Pro Gly Gly Gly Ser Asn Pro Arg Ser
        35                  40                  45

Val Pro Phe Glu Tyr Tyr Arg Ile Arg Lys Val Lys Val Glu Phe Trp
    50                  55                  60

Pro Cys Ser Pro Ile Thr Gln Gly Asp Arg Gly Val Gly Ser Thr Ala
65                  70                  75                  80

Val Ile Leu Asp Asp Asn Phe Val Thr Lys Ala Thr Ala Leu Thr Tyr
                85                  90                  95

Asp Pro Tyr Val Asn Tyr Ser Ser Arg His Thr Ile Thr Gln Pro Phe
            100                 105                 110

Ser Tyr His Ser Arg Tyr Phe Thr Pro Lys Pro Val Leu Asp Ser Thr
        115                 120                 125

Ile Asp Tyr Phe Gln Pro Asn Asn Lys Arg Asn Gln Leu Trp Leu Arg
    130                 135                 140

Leu Gln Thr Ala Gly Asn Val Asp His Val Gly Leu Gly Thr Ala Phe
145                 150                 155                 160
```

Glu Asn Ser Lys Tyr Asp Gln Glu Tyr Asn Ile Arg Val Thr Met Tyr
                165                 170                 175

Val Gln Phe Arg Glu Phe Asn Leu Lys Asp Pro Pro Leu Asn Pro
            180                 185                 190

<210> SEQ ID NO 4
<211> LENGTH: 232
<212> TYPE: PRT
<213> ORGANISM: Artificial Sequence
<220> FEATURE:
<223> OTHER INFORMATION: Fusion Polypeptide

<400> SEQUENCE: 4

Lys Thr Ile Ser Val Val Thr Leu Leu Cys Val Leu Pro Ala Val Val
1               5                   10                  15

Tyr Ser Thr Cys Thr Val Pro Thr Met Asn Asn Ala Lys Leu Thr Ser
            20                  25                  30

Thr Glu Thr Ser Trp Lys Lys Glu Lys Gly Val Leu Asn Thr Arg Leu
        35                  40                  45

Ser Arg Thr Phe Gly Tyr Thr Ile Lys Arg Thr Thr Val Lys Thr Pro
    50                  55                  60

Ser Trp Ala Val Asp Met Met Arg Phe Asn Ile Asn Asp Phe Val Pro
65                  70                  75                  80

Pro Gly Gly Gly Ser Asn Pro Arg Ser Val Pro Phe Glu Tyr Tyr Arg
                85                  90                  95

Ile Arg Lys Val Lys Val Glu Phe Trp Pro Cys Ser Pro Ile Thr Gln
            100                 105                 110

Gly Asp Arg Gly Val Gly Ser Thr Ala Val Ile Leu Asp Asp Asn Phe
        115                 120                 125

Val Thr Lys Ala Thr Ala Leu Thr Tyr Asp Pro Tyr Val Asn Tyr Ser
    130                 135                 140

Ser Arg His Thr Ile Thr Gln Pro Phe Ser Tyr His Ser Arg Tyr Phe
145                 150                 155                 160

Thr Pro Lys Pro Val Leu Asp Ser Thr Ile Asp Tyr Phe Gln Pro Asn
                165                 170                 175

Asn Lys Arg Asn Gln Leu Trp Leu Arg Leu Gln Thr Ala Gly Asn Val
            180                 185                 190

Asp His Val Gly Leu Gly Thr Ala Phe Glu Asn Ser Lys Tyr Asp Gln
        195                 200                 205

Glu Tyr Asn Ile Arg Val Thr Met Tyr Val Gln Phe Arg Glu Phe Asn
    210                 215                 220

Leu Lys Asp Pro Pro Leu Asn Pro
225                 230

<210> SEQ ID NO 5
<211> LENGTH: 702
<212> TYPE: DNA
<213> ORGANISM: Artificial Sequence
<220> FEATURE:
<223> OTHER INFORMATION: DNA encoding fusion polypeptide

<400> SEQUENCE: 5
atgaaaacga tttccgttgt tacgttgtta tgcgtactac ctgctgttgt ttattcaaca      60
tgtactgtac ccactatgaa taacgctaaa ttgacgtcta ccgaaacatc gtggaaaaaa     120
gagaaaggag tcttgaacac cagattgtct agaaccttcg gttacaccat taagagaacc     180

| | |
|---|---|
| accgtcaaaa cccatcttg ggctgtcgat atgatgagat tcaacatcaa cgatttcgtc | 240 |
| ccacctggtg gtggatcaaa ccctagatcc gttccattcg agtactacag aatcagaaaa | 300 |
| gtcaaagtcg agttctggcc atgctctcct attactcagg gtgatagagg agttggatca | 360 |
| actgccgtca tcttggatga caacttcgtc actaaggcta ctgccttgac ctacgatcct | 420 |
| tacgtcaatt actctagtag acacaccatc acccaaccat tctcatacca ttccagatac | 480 |
| ttcactccaa aacctgtctt ggactcaacc atcgattact ttcaaccaaa caacaagaga | 540 |
| aaccaattgt ggttgagatt gcaaactgcc ggtaacgtcg atcatgtcgg attgggaacc | 600 |
| gccttcgaaa actccaaata cgaccaggag tacaacatta gagtcaccat gtacgtccaa | 660 |
| ttcagagagt tcaacttgaa ggacccacca ttgaacccat aa | 702 |

<210> SEQ ID NO 6
<211> LENGTH: 182
<212> TYPE: DNA
<213> ORGANISM: Artificial Sequence
<220> FEATURE:
<223> OTHER INFORMATION: synthetic DNA

<400> SEQUENCE: 6

| | |
|---|---|
| ggatccacca tgaaaacgat ttccgttgtt acgttgttat gcgtactacc tgctgttgtt | 60 |
| tattcaacat gtactgtacc cactatgaat aacgctaaat tgacgtctac cgaaacatcg | 120 |
| tggaaaaaag agaaggagt cttgaacacc agattgtcta gacattgaac ccataagtcg | 180 |
| ac | 182 |

<210> SEQ ID NO 7
<211> LENGTH: 561
<212> TYPE: DNA
<213> ORGANISM: Artificial Sequence
<220> FEATURE:
<223> OTHER INFORMATION: synthetic DNA

<400> SEQUENCE: 7

| | |
|---|---|
| tctagaacct tcggttacac cattaagaga accaccgtca aaaccccatc ttgggctgtc | 60 |
| gatatgatga gattcaacat caacgatttc gtcccacctg gtggtggatc aaaccctaga | 120 |
| tccgttccat tcgagtacta cagaatcaga aaagtcaaag tcgagttctg gccatgctct | 180 |
| cctattactc agggtgatag aggagttgga tcaactgccg tcatcttgga tgacaacttc | 240 |
| gtcactaagg ctactgcctt gacctacgat ccttacgtca attactctag tagacacacc | 300 |
| atcacccaac cattctcata ccattccaga tacttcactc caaaacctgt cttggactca | 360 |
| accatcgatt actttcaacc aaacaacaag agaaaccaat tgtggttgag attgcaaact | 420 |
| gccggtaacg tcgatcatgt cggattggga accgccttcg aaaactccaa atacgaccag | 480 |
| gagtacaaca ttagagtcac catgtacgtc caattcagag agttcaactt gaaggaccca | 540 |
| ccattgaacc cataagtcga c | 561 |

<210> SEQ ID NO 8
<211> LENGTH: 19
<212> TYPE: DNA
<213> ORGANISM: Artificial Sequence
<220> FEATURE:
<223> OTHER INFORMATION: Primer

<400> SEQUENCE: 8

| | |
|---|---|
| aatattacgg gtgctgtttt | 19 |

<210> SEQ ID NO 9
<211> LENGTH: 18
<212> TYPE: DNA
<213> ORGANISM: Artificial Sequence
<220> FEATURE:
<223> OTHER INFORMATION: Primer

<400> SEQUENCE: 9
aaaaacatcg tattcctg                                                    18

<210> SEQ ID NO 10
<211> LENGTH: 30
<212> TYPE: DNA
<213> ORGANISM: Artificial Sequence
<220> FEATURE:
<223> OTHER INFORMATION: Primer

<400> SEQUENCE: 10
cgttcatgtt aagcttaacc tgaaatattg                                        30

<210> SEQ ID NO 11
<211> LENGTH: 33
<212> TYPE: DNA
<213> ORGANISM: Artificial Sequence
<220> FEATURE:
<223> OTHER INFORMATION: Primer

<400> SEQUENCE: 11
gtttaaacga attcggtacc cttaaaaaca tcg                                    33

<210> SEQ ID NO 12
<211> LENGTH: 36
<212> TYPE: DNA
<213> ORGANISM: Artificial Sequence
<220> FEATURE:
<223> OTHER INFORMATION: Primer

<400> SEQUENCE: 12
cgccgagctc gagaatatta cgggtgctgt ttttac                                 36

<210> SEQ ID NO 13
<211> LENGTH: 33
<212> TYPE: DNA
<213> ORGANISM: Artificial Sequence
<220> FEATURE:
<223> OTHER INFORMATION: Primer

<400> SEQUENCE: 13
ccagactgca gagaacatag gtcctaatat aag                                    33

<210> SEQ ID NO 14
<211> LENGTH: 46
<212> TYPE: DNA
<213> ORGANISM: Artificial Sequence
<220> FEATURE:
<223> OTHER INFORMATION: synthetic oligonucleotide

<400> SEQUENCE: 14
aattgcccgg gtaccgtcga tcgactttttt atggcccccc cggcca                    46

<210> SEQ ID NO 15
<211> LENGTH: 46
<212> TYPE: DNA
<213> ORGANISM: Artificial Sequence
<220> FEATURE:
<223> OTHER INFORMATION: synthetic oligonucleotide

```
<400> SEQUENCE: 15
agcttggccg ggggggccat aaaaagtcga tcgacggtac ccgggc              46

<210> SEQ ID NO 16
<211> LENGTH: 719
<212> TYPE: DNA
<213> ORGANISM: Artificial Sequence
<220> FEATURE:
<223> OTHER INFORMATION: DNA encoding ORF2

<400> SEQUENCE: 16
ggatccacca tgacgtatcc aaggaggcgt taccggagaa gaagacaccg cccccgcagc    60
catcttggcc agatcctccg ccgccgcccc tggctcgtcc accccgcca ccgttaccgc    120 tggagaagga aaaatggcat cttcaacacc cgcctctccc gcaccttcgg atatactgtc   180
aagcgaacca cagtcagaac gccctcctgg gcggtgaca tgatgagatt caatattaat    240
gactttcttc ccccaggagg gggctcaaac cccgctctg tgcctttga atactacaga    300 ataagaaagg ttaaggttga attctggccc tgctccccga tcacccaggg tgacagggga   360
gtgggctcca gtgctgttat tctagatgat aactttgtaa caaaggccac agccctcacc   420
tatgacccct atgtaaacta ctcctcccgc ataccataa cccagccctt ctcctaccac    480
tcccgctact ttacccccaa acctgtccta gattccacta ttgattactt ccaaccaaac   540
aacaaaagaa accagctgtg gctgagacta caaactgctg gaaatgtaga ccacgtaggc   600
ctcggcactg cgttcgaaaa cagtatatac gaccaggaat acaatatccg tgtaaccatg   660
tatgtacaat tcagagaatt taatcttaaa gacccccac ttaacccta atagtcgac     719

<210> SEQ ID NO 17
<211> LENGTH: 25
<212> TYPE: DNA
<213> ORGANISM: Artificial Sequence
<220> FEATURE:
<223> OTHER INFORMATION: Primer

<400> SEQUENCE: 17
ggtggtggat ccaaccctag atccg                                        25

<210> SEQ ID NO 18
<211> LENGTH: 27
<212> TYPE: DNA
<213> ORGANISM: Artificial Sequence
<220> FEATURE:
<223> OTHER INFORMATION: Primer

<400> SEQUENCE: 18
ggtgggtcga ccaagttgaa ctctctg                                      27
```

FUSION POLYPEPTIDES AND VACCINES

CROSS-REFERENCE TO RELATED APPLICATION

This application is the U.S. national stage application of International Patent Application No. PCT/EP2014/057287, filed Apr. 10, 2014.

The Sequence Listing for this application is labeled "Seq-List.txt" which was created on Oct. 6, 2015 and is 10 KB. The entire contents of the sequence listing is incorporated herein by reference in its entirety.

The present invention relates to novel immunogenic polypeptides and their use in vaccine compositions. The invention also relates to nucleic acids, vectors and cells which express the polypeptides and the uses thereof. The polypeptides of the invention more specifically comprise an immunogenic domain and a cell membrane addressing domain which is derived from a B5R gene. The invention is particularly suited to produce vaccines for non-human animals, particularly for vaccinating swine against PCV2 infection.

BACKGROUND

Porcine circovirus (PCV) was originally identified as a contaminant of porcine kidney cell cultures (PK15 ATCC CCL-33). The PCV virion has been characterized as being an icosahedral, non-enveloped virus with a single-stranded circular DNA of about 1.76 kb. PCV was classified in the genus Circovirus of the Circoviridae family, which consists of other animal circoviruses such as psittacine beak-feather disease virus, goose circovirus, canary circovirus, and pigeon circovirus. Two genotypes of PCV have been recognized. The PK15 cell-derived PCV has been considered to be nonpathogenic to pigs, and is designated PCV type 1 (PCV1). On the other hand, PCV type 2 (PCV2) has been accepted as the major infectious agent involved in several pig diseases. PCV2 associated diseases cause significant economic losses to swine producers worldwide. PCV2 associated diseases are described in WO2007/076520 and include, for example, Postweaning Multisystemic Wasting Syndrome (PMWS), Porcine Dermatitis and Nephropathy Syndrome (PDNS), Porcine Respiratory Disease Complex (PRDC), reproductive disorders, granulomatous enteritis, exudative epidermitis, necrotizing lymphadenitis, and congenital tremors. Occurrences of PCV2 subtype A (PCV2A) and PCV2 subtype B (PCV2B) have been reported particularly in 2000 in West Europe and in Central Europe in 2003. More recently similar changes have been reported in 2008 in wild boars.

Currently developed PCV2 vaccines, such as Circovac® (Merial), Ingelvac®, CircoFLEX (Boehringer Ingelheim Vetmedica), or Suvaxyn®, are either inactivated PCV2 vaccines or Sub-Unit vaccines. Regarding inactivated PCV2 vaccines, current PCV2 strains subtype A or B present several weaknesses. Particularly, PCV2 viruses can only be produced at low titers, generally less than $10^5$ TCID50 viral particles per ml. Also, these viruses cannot be maintained in tissue cultures and permanently infected cell lines. Regarding PCV2 Sub-Unit vaccines, they typically use a purified, recombinant PCV2 capsid protein produced by expression of the ORF2 gene of PCV2 in a baculovirus system. In this regard, the protein encoded by ORF2 of PCV2 isolates Imp1011 has been reported in EP1741785. A protein encoded by ORF2 of PCV2 isolate PCV2Rm has been reported in WO2010/061000. The protein encoded by ORF2 of PCV2 isolate 412 has been reported in EP1816200. Another protein encoded by an ORF2 of a further PCV2 isolate has been reported in EP1036180 or EP2225367.

Expression efficiency and immunogenicity of these natural capsid proteins are, however, not optimal and do not always provide the required level of immune protection in vaccinated animals. In particular, the ORF2 protein comprises a nuclear localization sequence which leads to expression of the protein in the nucleus of the cells. Such intracellular localization does not facilitate extraction or purification of the protein and could also prevent or reduce the effectiveness of DNA or vector vaccines which express the ORF2 protein in vivo in the animals.

WO2010/068969 proposes to modify the expression profile of ORF2 to express an ORF2 antigen in soluble form by using foreign secretion signal peptide sequences. In this application, it is proposed to fuse ORF2 to a secretion signal or to a cell membrane signal, and to include in the construct a cleavage site so that the soluble ORF2 can be released in soluble form. This application proposes a long prophetic list of potential candidate secretory peptides. However, the application does not contain any experimental data showing that effective or improved expression/immunogenicity may be obtained by modifying the expression profile of an ORF2. No construct is disclosed allowing effective immunization.

The present invention proposes novel improved constructs for expressing antigenic polypeptides. The present invention discloses fusion products that are specifically adapted for the improved expression of antigenic polypeptides at the cell surface, especially using a viral expression vector such as a swinepox virus.

The invention shows that by expressing an antigenic polypeptide at the surface of infected/transduced cells using a B5R-derived addressing signal, an improved immune response is obtained, causing effective protection. By presenting the antigen at the cell surface in vivo in the animal, the vaccines of the invention most effectively deliver and expose the antigen to the immune system, particularly to immune cells such as lymphocytes, dendritic cells and macrophages. By presenting the antigen at the cell surface, the invention provides the immunogen in an active conformation to elicit a potent protective immune response. The invention may be applied to any antigenic polypeptide, particularly viral antigens.

SUMMARY OF THE INVENTION

The present application provides a polypeptide comprising a signal peptide derived from the B5R gene of a Vaccinia virus operably linked to a heterologous antigenic polypeptide.

In a particular embodiment, the signal peptide comprises SEQ ID NO: 1 or a sequence having at least 90% identity to SEQ ID NO: 1. The antigenic polypeptide may be a viral, bacterial or parasite antigen. It is preferably a viral antigen, more particularly a capsid protein or an immunogenic domain thereof.

In a particular embodiment, the antigenic polypeptide is an ORF2 of a PCV2 virus, or an antigenic domain thereof. A preferred embodiment uses an antigenic polypeptide which comprises the sequence of SEQ ID NO: 3 or a sequence having at least 80% identity to SEQ ID NO: 3.

The polypeptide of the invention may be synthetic or recombinant, and may comprise post-transcriptional modifications such as glycosylation, added chemical groups, etc. Most preferably, the polypeptide of the invention is devoid of a cleavage site between the addressing peptide and the antigenic peptide.

Another object of the invention is a cell expressing on its surface a polypeptide as defined above.

A further object of the invention relates to a nucleic acid encoding a polypeptide as defined above.

Another object of the invention is a vector comprising a nucleic acid of the invention. Preferably, the vector is a viral vector, such as most preferably a pseudorabies virus (PRV) or a swinepox virus (SPV). The use of a swinepox is particularly advantageous since B5R signal peptide derived from a Vaccinia virus having improved compatibility with swinepox.

A further object of the invention resides in a composition comprising a polypeptide, a cell, a nucleic acid, or a vector as defined above.

A further object of the invention is a vaccine comprising a polypeptide, a cell, a nucleic acid, or a vector as defined above and, optionally, an adjuvant.

The present invention also relates to methods of immunizing or inducing an immune response in non-human animals (e.g., pigs) comprising administering to said animal a polypeptide, nucleic acid, cell, vector or vaccine as described above.

The present invention also relates to methods of treating and/or preventing PCV2 associated diseases in non-human animals (e.g., pigs) comprising administering to said animal a polypeptide, nucleic acid, cell, vector or vaccine as described above.

The invention also relates to the use of a signal peptide derived from the B5R gene of a Vaccinia virus for the expression of a heterologous antigenic polypeptide in a cell.

The invention may be used to induce an immune response and/or to vaccinate any non-human animal. It is particularly useful to vaccinate swine against PCV2 infection or PCV2-diseases.

FIG. 3: IFA of SPV-infected cells. ESK-4 cells were infected with rSPV (SVR3 or SVR7) or parental SPV. Five days later, infected cells were treated with acetone/methanol (a) or none (b), and reacted with $1^{st}$ antibodies [Rabbit anti-β-Galactosidase (α-βGal) and Rat anti-PCV2-ORF2 (α-ORF2) (1:1000)] and $2^{nd}$ antibodies [Goat anti-rabbit IgG Alexa Fluor 488 and anti-Rat IgG Alexa Fluor 546 (1:1000)].

FIG. 4: Serological IF titers against PCV2. Rm40-infected RPL-2 cells were coated on each well of 96-well plates. Cells were fixed with acetone/methanol, and two-fold dilutions of sera were incubated for 1 hr after blocking (0.5% Non-Fat milk in PBS). Anti-pig IgG-FITC antibody produced in rabbit (SIGMA Cat. #: F1638, 1:1000) were used as secondary antibodies. IF titer of the standard positive pig serum, PAB-PCV2 (VMRD) was 2560.

DETAILED DESCRIPTION OF THE INVENTION

The present invention relates to novel immunogenic polypeptides and the uses thereof, particularly in vaccine compositions. The invention also relates to nucleic acids, vectors and cells which express the polypeptides and the uses thereof. The polypeptides of the invention more specifically comprise an immunogenic domain and a cell membrane addressing domain that are operably linked, wherein the cell membrane addressing domain is derived from a B5R gene. The invention is particularly suited to produce vaccines for non-human animals, particularly for vaccinating swine against PCV2 infection.

Cell-Membrane Addressing Peptide Derived from B5R

The term "derived from" indicates that the sequence of the addressing peptide is identical to or substantially similar to the sequence of the signal peptide of a B5R gene of a Vaccinia virus. In a preferred embodiment, the addressing peptide comprises a sequence having at least 90% identity to the sequence of the signal peptide of a B5R gene of a Vaccinia virus, even more preferably at least 91, 92, 93, 94, 95, 96, 97, 98 or 99% sequence identity.

A most preferred example of a sequence of a signal peptide of a B5R gene is SEQ ID NO: 1 or a sequence having at least 90% identity to SEQ ID NO: 1, more preferably at least 91, 92, 93, 94, 95, 96, 97, 98 or 99% identity to SEQ ID NO: 1. Accordingly, in a particular embodiment, the polypeptide of the invention comprises a signal peptide sequence which comprises SEQ ID NO: 1 or a sequence having at least 90% identity to SEQ ID NO: 1.

The signal peptide may comprise further amino acids derived from the B5R gene, as long as these amino acids do not alter the membrane-addressing properties of the peptide. In this regard, in a particular embodiment, the signal peptide comprises SEQ ID NO: 2. Amino acids 23-36 of SEQ ID NO: 2 do not substantially participate in the membrane-addressing function. However, the results presented show that these amino acids facilitate stabilization and proper conformation of the fusion polypeptide.

Alternatively, or in addition, the signal peptide may comprise further amino acids which are not derived from the B5R gene, as long as these amino acids do not alter the membrane-addressing properties of the peptide. These amino acids may have cloning utility (e.g. restriction sites, for instance), or may participate in the stability of the polypeptide.

Preferably, the signal peptide does not comprise more than 100 amino acids, even more preferably not more than 50 amino acids.

As indicated above, the invention includes signal peptides comprising a sequence having at least 90% identity to SEQ ID NO: 1 or 2. The degree of homology between two amino acid or nucleic acid sequences may be determined by means of computer programs known per se in the art such as GAP provided in the GCG program package (Program Manual for the Wisconsin Package, Version 8, August 1996, Genetics Computer Group, 575 Science Drive, Madison, Wis., USA 53711) (Needleman, S. B. and Wunsch, C D., (1970), Journal of Molecular Biology, 48, 443-453). Using GAP with the following settings for DNA sequence comparison: GAP creation penalty of 5.0 and GAP extension penalty of 0.3. Nucleic acid/amino acid molecules may be aligned to each other using the Pileup alignment software, available as part of the GCG program package, using, for instance, the default settings of gap creation penalty of 5 and gap width penalty of 0.3.

Suitable experimental conditions for determining whether a given nucleic acid molecule hybridizes to a specified nucleic acid may involve pre-soaking of a filter containing a relevant sample of the nucleic acid to be examined in 5×SSC for 10 minutes, and pre-hybridisation of the filter in a solution of 5×SSC, 5×Denhardt's solution, 0.5% SDS and 100 [mu]g/ml of denatured sonicated salmon sperm DNA, followed by hybridisation in the same solution containing a concentration of 10 ng/ml of a P-dCTP-labeled probe for 12 hours at approximately 45° C., in accordance with the hybridisation methods as described in Sambrook et al. (1989; Molecular Cloning, A Laboratory Manual, 2nd edition, Cold Spring Harbour, N.Y.). The filter is then washed twice for 30 minutes in 2×SSC, 0.5% SDS at least 55° C. (low stringency), at least 60° C. (medium stringency), at least 65° C. (medium/high stringency), at least 70° C. (high stringency), or at least 75° C. (very high stringency). Hybridization may be detected by exposure of the filter to an x-ray film.

In a preferred embodiment, the peptide signal comprises SEQ ID NO: 1 or 2.

In a particular embodiment, the peptide signal consists of SEQ ID NO: 1 or 2.

Antigenic Polypeptides

The invention may be used with any antigenic polypeptide, i.e., with any polypeptide comprising one or more epitopes that can cause an immune response. The polypeptide may be an entire protein, a fragment of a protein, or a small peptide of, for instance 10 amino acids. Preferably, the antigenic polypeptide comprises less than about 500 amino acids.

The antigenic polypeptide is "heterologous" with respect to the signal peptide, which means that the antigenic polypeptide is not naturally associated with the signal peptide in nature. Typically, the antigenic polypeptide is not the sequence of a B5R protein. The term heterologous indicates, for instance, that the antigenic polypeptide is from a virus distinct from a Vaccinia virus, or from a protein distinct from a B5R protein, for instance.

The antigenic polypeptide may be an antigenic polypeptide of a viral, cellular (e.g., bacterial) or parasitic agent.

In this regard, as indicated above, in a preferred embodiment, the antigenic polypeptide is an ORF2 protein of a PCV2 virus, or an antigenic domain thereof.

The ORF2 protein of PCV2 isolate Imp1011 has been reported in EP1741785. The ORF2 protein of PCV2 isolate PCV2Rm has been reported in WO2010/061000. The ORF2 protein of PCV2 isolate 412 has been reported in EP1816200. Another ORF2 protein of a further PCV2 isolate has been reported in EP1036180 or EP2225367. All of these ORF2 proteins are contemplated for use in the present invention.

In a preferred embodiment, the ORF2 protein for use in the invention comprises SEQ ID NO: 3 or any sequence having at least 80% identity to SEQ ID NO: 3, even more preferably at least 82, 84, 86, 88, 90, 91, 92, 93, 94, 95, 96, 97, 98, or 99% identity to SEQ ID NO: 3.

Typically, PCV2 ORF2 proteins comprise about 234 amino acids. The sequence comprises a nuclear localization sequence, which generally corresponds to amino acids 1-42 of the sequence.

It is preferred, for the present invention, to use a portion of an ORF2 protein which is devoid of the native nuclear localization sequence (i.e., the sequence at residues 1 to 42 of a native ORF2), and to replace this sequence by the membrane-addressing peptide. SEQ ID NO: 3 is an amino acid sequence of an ORF2 protein devoid of nuclear localization sequence.

Sequence having identity to SEQ ID NO: 3 and retaining PCV2 immunogenic activity may be derived artificially or obtained from PCV2 serotypes listed above, or from further distinct serotypes. Typically, the first 42 amino acids of the ORF2 protein are removed to suppress the nuclear-localization function.

As indicated, the invention may be used with immunogenic polypeptides of other viral or pathogenic antigens such as, for instance, any protein (e.g., glycoprotein, capsid protein, or antigen fragment thereof) of a virus or pathogen selected from e.g., *Actinobacillus pleuropneunomia*; Adenovirus; Alphavirus such as Eastern equine encephalomyelitis viruses; *Balantidium coli*; *Bordetella bronchiseptica*; *Brachyspira* spp., preferably *B. hyodyentheriae*, *B. pilosicoli*, *B. innocens*, *Brucella suis*, preferably biovars 1, 2 and 3; Classical swine fever virus, African swine fever virus; *Chlamydia* and *Chlamydophila* spp. and preferably *C. pecorum* and *C. abortus*; *Clostridium* spp., preferably *Cl. difficile*, *Cl. perfringens* types A, B and C, *Cl. novyi*, *Cl. septicum*, *Cl. tetani*; Digestive and respiratory Coronavirus; *Cryptosporidium parvum*; *Eimeria* spp; *Eperythrozoonis suis* currently named *Mycoplasma haemosuis*; *Erysipelothrix rhusiopathiae*; *Escherichia coli*; *Haemophilus parasuis*, preferably subtypes 1, 7 and 14; Hemagglutinating encephalomyelitis virus; lsospora suis; Japanese Encephalitis virus; *Lawsonia intracellulars*; *Leptospira* spp., preferably *Leptospira australis*, *Leptospira canicola*, *Leptospira grippotyphosa*, *Leptospira icterohaemorrhagicae*, *Leptospira interrogans*, *Leptospira Pomona* and *Leptospira tarassovi*; *Mannheimia haemolytica*; *Mycobacterium* spp., preferably *M. avium*, *M. intracellular* and *M. bovis: Mycoplasma hyponeumoniae*; Parvovirus; *Pasteurella multocida*; Porcine cytomegolovirus; Porcine parovirus, Porcine reproductive and respiratory syndrome virus: Pseudorabies virus; Rotavirus; Sagiyama virus; *Salmonella* spp., preferably *S. thyhimurium* and *S. choleraesuis*; *Staphylococcus* spp., preferably *S. hyicus*; *Streptococcus* spp., preferably Strep suis; Swine cytomegalovirus; Swine herpes virus; Swine influenza virus; Swinepox virus; *Toxoplasma gondii*; Vesicular stomatitis virus or virus of exanthema of swine; or other isolates and subtypes of porcine circovirus.

Polypeptide Assembling and Production

The polypeptide of the invention generally comprises a cell membrane-addressing peptide operably linked to an antigenic polypeptide. The term "operably linked" indicates that the two domains are fused to each other, directly or indirectly, in a manner which allows addressing of the polypeptide to a cell membrane and expression of the antigenic polypeptide outside of a cell.

Most preferably, the cell membrane-addressing peptide is located N-terminally and the immunogenic polypeptide is located C-terminally. Both domains are covalently linked, preferably by an amino bond. Accordingly, the polypeptide of the invention preferably comprises, from N→C-ter:
 the cell membrane-addressing peptide,
 the immunogenic polypeptide The polypeptide may further comprise additional domains or sequences. For instance, the polypeptide may comprise a linker sequence between the cell membrane-addressing peptide and the immunogenic polypeptide. Preferably, however, the two domains are directly linked without a linker sequence. Also, in a preferred embodiment, the polypeptide is devoid of a cleavage site so that the immunogenic polypeptide is exposed at the cell surface and essentially not released in soluble form.

A preferred and specific example of a polypeptide of the invention comprises the amino acid sequence of SEQ ID NO: 4.

The polypeptide of the invention may further comprise an N-ter methionine residue.

The polypeptide of the invention may be glycosylated.

The polypeptides of the invention may be produced by a synthetic process, or by recombinant means. Preferably, the polypeptides of the invention are engineered to be produced/expressed directly in cells or whole organisms by expression of a coding nucleic acid molecule. Indeed, the new expression profile of the polypeptides of the invention is particularly adapted for the design of DNA or vector vaccines, which comprise a nucleic acid molecule encoding a polypeptide of the invention. Upon introduction into an organism, the nucleic acid enters cells and expresses the polypeptide which becomes exposed at the cell surface and exhibits improved immunogenicity. As will be discussed below, the nucleic acid may be naked, or formulated with any suitable vector. Alternatively, the invention may use cell vaccines, wherein the polypeptide is expressed in culture at the surface of cells and the resulting cells are used as a vaccine composition.

The invention therefore also encompasses and utilizes nucleic acid molecules encoding polypeptides as defined above.

Nucleic Acid

A further object of the invention relates to a nucleic acid molecule encoding a polypeptide as defined above. The nucleic acid may be used to produce the polypeptide in vitro, or to produce cells expressing the polypeptide on their surface, or to produce vaccines wherein the active agent is the nucleic acid or a vector containing the nucleic acid.

The nucleic acid of the invention may be DNA or RNA, single- or double-stranded. The nucleic acid is typically cDNA or RNA. The nucleic acid may be produced by techniques well known in the art, such as synthesis, or cloning, or amplification of the sequence encoding the immunogenic polypeptide; synthesis, or cloning, or amplification of the sequence encoding the cell membrane addressing sequence; ligation of the sequences and their cloning/amplification in appropriate vectors and cells.

In a particular embodiment, the invention relates to a nucleic acid molecule comprising SEQ ID NO: 5.

Vector

The nucleic acid molecules according to the invention may be provided in the form of a nucleic acid molecule per se such as naked nucleic acid molecules; a vector; virus or host cell etc, either from prokaryotic or eukaryotic origin. Vectors include expression vectors that contain a nucleic acid molecule of the invention. The vectors of the present invention may, for example, comprise a transcriptional promoter, and/or a transcriptional terminator, wherein the promoter is operably linked with the nucleic acid molecule, and wherein the nucleic acid molecule is operably linked with the transcription terminator.

In this regard, a particular object of the invention is a viral vector comprising a nucleic acid as defined above. The viral vector may be derived from different types of viruses, such as, preferably, Swinepox, Fowlpox, Pseudorabies, Aujezky's virus, *salmonella*, vaccinia virus, BHV (Bovine Herpes Virus), HVT (Herpes Virus of Turkey), adenovirus, TGEV (Transmissible Gastroenteritidis Coronavirus), Erythrovirus, and SIV (Simian Immunodeficiency Virus).

In a preferred embodiment, the vector is a recombinant swinepox virus. Swinepox virus (SPV) is only mildly pathogenic in swine, and elicits a protective immune response. So, SPV is an excellent candidate for a viral vector in swine. The general procedure for creation of recombinant SPV was described in several references (Vet Rec. 1994 Jan. 1; 134(1):13-8). In a typical method, the first step in the construction of a recombinant SPV is to create homology plasmids that can direct the insertion of the transcriptional unit(s) for antigenic polypeptide gene of this invention into the SPV genome. Insertion occurs by homologous recombination and thus requires that the inserted DNA be flanked by a contiguous SPV genomic region. In the case of SPV recombinants, the thymidine kinase (TK) gene was selected firstly as the insertion site and proved to be non-essential region for virus replication. Because the transcriptional machinery of poxvirus will not recognize host cell promoters, the antigenic polypeptide gene of this invention is preferably linked to poxvirus promoters. Vaccinia virus promoters such as P11 or P7.5 are preferred for expression in a recombinant SPV, but other poxvirus promoters may be used. Once the homology plasmid has been generated, it is transfected into competent cells such as embryonic swine kidney (ESK-4) or pig kidney (PK-15) cells that have been previously infected with SPV. Recombinants are generated by homologous recombination between the replicating SPV genomes and the transfected plasmid. The recombinant SPV can be selected/screened using conventional techniques. One method of identification utilizes the *Escherichia coli* lacZ gene as a marker. In this case, a chromogenic substrate, 5-bromo-4-chloro-3-indolyl β-D-galactoside (X-gal), which is converted to a blue compound by the action of the expressed enzyme (β-galactosidase) is then used to identify the virus plaques produced by the recombinant virus in the progeny against a background of colorless plaques generated by non-recombinant viruses. In the case of no marker gene, the production of the antigenic polypeptide expressed by recombinant SPV can be verified by using specific antibodies against the antigenic polypeptide in an immunofluorescence assay. Using the above-mentioned protocols, recombinant SPV expressing the antigenic polypeptide of this invention can be generated.

Other expression systems and vectors may be used as well, such as plasmids that replicate and/or integrate in yeast cells.

The invention also relates to a method for preparing a polypeptide of the invention, the method comprising culturing a host cell containing a nucleic acid or vector as defined above under conditions suitable for expression of the nucleic acid and recovering the polypeptide. As indicated above, the proteins and peptides may be purified according to techniques known per se in the art. The invention also provides expression kits comprising (a) a host cell (preferably insect cells or yeast cells), (b) means of expressing a polypeptide of the invention, e.g. comprising a vector system capable of being replicated in said cell, and (c) means of recovering the protein or peptide of the invention.

Vaccine Compositions

The term "vaccine" as used herein includes an agent which may be used to cause, stimulate or amplify the immune system of animals (e.g., pigs) against a pathogen. Vaccines of the invention are able to cause or stimulate or amplify immunity against a PCV2 virus.

The term "immunization" includes the process of delivering an immunogen to a subject. Immunization may, for example, enable a continuing high level of antibody and/or cellular response in which T-lymphocytes can kill or suppress the pathogen in the immunized non human animal, such as pig, which is directed against a pathogen or antigen to which the animal has been previously exposed.

Vaccines of the invention comprise an immunologically effective amount of a polypeptide, cell or nucleic acid as described above in a pharmaceutically acceptable vehicle. As a result of the vaccination with a composition of the invention, animals become at least partially or completely immune to PCV2 infections, or resistant to developing moderate or severe PCV2 infections. PCV2 vaccines may be used to elicit a humoral and/or a cellular response.

PCV2 infections or associated diseases include inter alia Postweaning Multisystemic Wasting Syndrome (PMWS), Porcine Dermatitis and Nephropathy Syndrome (PDNS), Porcine Respiratory Disease Complex (PRDC), reproductive disorders, granulomatousenteritis, exudative epidermitis, necrotizing lymphadenitis, and congenital tremors. Preferably, a non human animal subject, such as a pig, is protected to an extent to which one to all of the adverse physiological symptoms or effects of PCV2 infections are significantly reduced, ameliorated or totally prevented.

The present invention also relates to a combination vaccine comprising a polypeptide, nucleic acid or cell of the invention in combination with at least one additional protein antigen [Gupi P. S. Nayar et al. (Can. Vet. J, vol. 38, 1997: 385-387) and Clark E. G. (Proc. Am. Assoc. Swine Prac. 1997; 499-501)].

In practice, the exact amount required for an immunologically effective dose may vary from subject to subject depending on factors such as the age and general condition of the subject, the nature of the formulation and the mode of administration. An appropriate "effective amount" may be determined by one of ordinary skill in the art using only routine experimentation. For instance, methods are known in the art for determining or titrating suitable dosages of a vaccine to find minimal effective dosages based on the weight of the non human animal subject, concentration of the vaccine and other typical factors.

In a typical embodiment, the vaccine comprises a unitary dose of between 0.1-50 µg, preferably between 0.1 and 25, even more preferably of between 1 and 15 µg, typically approx. 10 µg, of polypeptide or nucleic acid antigen of the invention.

The dosage of the vaccine, concentration of components therein and timing of administering the vaccine, which elicit a suitable immune response, can be determined by methods such as by antibody titrations of sera, e.g., by ELISA and/or seroneutralization assay analysis and/or by vaccination challenge evaluation.

In a particular embodiment, the vaccine comprises the polypeptide of the invention in purified form, optionally in combination with any suitable excipient or carrier.

In another particular embodiment, the vaccine comprises a nucleic acid as defined above, optionally in combination with any suitable excipient or carrier. A most preferred vaccine comprises a viral vector containing a nucleic acid as defined above. A further preferred vaccine comprises a swinepox virus which comprises a nucleic acid as defined above.

Vaccines may comprise other ingredients, known per se by one of ordinary skill in the art, such as pharmaceutically acceptable carriers, excipients, diluents, adjuvants, freeze drying stabilizers, wetting or emulsifying agents, pH buffering agents, gelling or viscosity enhancing additives, and preservatives, depending on the route of administration.

Examples of pharmaceutically acceptable carriers, excipients or diluents include, but are not limited to demineralised or distilled water; saline solution; vegetable based oils such as peanut oil, *arachis* oil, safflower oil, olive oil, cottonseed oil, maize oil, sesame oil, or coconut oil; silicone oils, including polysiloxanes, such as methyl polysiloxane, phenyl polysiloxane and methylphenyl polysolpoxane; volatile silicones; mineral oils such as light liquid paraffin oil, or heavy liquid paraffin oil; squalene; cellulose derivatives such as methylcellulose, ethylcellulose, carboxymethylcellulose, carboxymethylcellulose sodium salt, or hydroxypropyl methylcellulose; lower alkanols, for example ethanol or isopropanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrrolidone; agar; carrageenan; gum tragacanth or gum acacia; and petroleum jelly. Typically, the carrier or carriers will form from 10% to 99.9% by weight of the vaccine composition and may be buffered by conventional methods using reagents known in the art, such as sodium hydrogen phosphate, sodium dihydrogen phosphate, potassium hydrogen phosphate, potassium dihydrogen phosphate, a mixture thereof, and the like.

Examples of adjuvants include, but are not limited to, oil in water emulsions, aluminum hydroxide (alum), immunostimulating complexes, non-ionic block polymers or copolymers, cytokines (like IL-1, IL-2, IL-7, IFN-α, IFN-β, IFN-γ, etc.), saponins, monophosphoryl lipid A (MLA), muramyl dipeptides (MDP) and the like. Other suitable adjuvants include, for example, aluminum potassium sulfate, heat-labile or heat-stable enterotoxin(s) isolated from *Escherichia coli*, cholera toxin or the B subunit thereof, diphtheria toxin, tetanus toxin, pertussis toxin, Freund's incomplete or complete adjuvant, etc. Toxin-based adjuvants, such as diphtheria toxin, tetanus toxin and pertussis toxin may be inactivated prior to use, for example, by treatment with formaldehyde.

Examples of freeze-drying stabilizer may be for example carbohydrates such as sorbitol, mannitol, starch, sucrose, dextran or glucose, proteins such as albumin or casein, and derivatives thereof.

Vaccines may additionally comprise at least one immunogen from at least one additional pathogen, e.g., a pig pathogen such as *Actinobacillus pleuropneunomia*; Adenovirus; Alphavirus such as Eastern equine encephalomyelitis viruses; *Balantidium coli; Bordetella bronchiseptica; Brachyspira* spp., preferably *B. hyodyentheriae, B. pilosicoli, B. innocens, Brucella suis*, preferably biovars 1, 2 and 3; Classical swine fever virus, African swine fever virus; *Chlamydia* and *Chlamydophila* spp., preferably *C. pecorum* and *C. abortus; Clostridium* spp., preferably *Cl. difficile, Cl. perfringens* types A, B and C, *Cl. novyi, Cl. septicum, Cl. tetani*; Digestive and respiratory Coronavirus; *Cryptosporidium parvum; Eimeria* spp.; *Eperythrozoonis suis* currently named *Mycoplasma* haemosuis; *Erysipelothrix rhusiopathiae; Escherichia coli; Haemophilus parasuis*, preferably subtypes 1, 7 and 14; Hemagglutinating encephalomyelitis virus; lsospora suis; Japanese Encephalitis virus; *Lawsonia intracellulars; Leptospira* spp., preferably *Leptospira australis, Leptospira canicola, Leptospira grippotyphosa, Leptospira icterohaemorrhagicae, Leptospira interrogans, Leptospira Pomona* and *Leptospira tarassovi; Mannheimia haemolytica; Mycobacterium* spp., preferably *M. avium, M. intracellular* and *M. bovis: Mycoplasma hyponeumoniae*; Parvovirus; *Pasteurella multocida*; Porcine cytomegolovirus; Porcine parovirus, Porcine reproductive and respiratory syndrome virus: Pseudorabies virus; Rotavirus; Sagiyama virus; *Salmonella* spp., preferably *S. thyhimurium* and *S. choleraesuis; Staphylococcus* spp., preferably *S. hyicus; Streptococcus* spp., preferably Strep suis; Swine cytomegalovirus; Swine herpes virus; Swine influenza virus; Swinepox virus; *Toxoplasma gondii*; Vesicular stomatitis virus and virus of exanthema of swine; or other isolates and subtypes of porcine circovirus.

The vaccine compositions of the invention may be liquid formulations such as an aqueous solution, water-in-oil or oil-in-water emulsion, syrup, an elixir, a tincture, or a preparation for parenteral, subcutaneous, intradermal, intramuscular or intravenous administration (e.g., injectable administration), such as sterile suspensions or emulsions. Such formulations are known in the art and are typically prepared by dissolution of the antigen and other typical additives in the appropriate carrier or solvent systems. Liquid formulations also may include suspensions and emulsions that contain suspending or emulsifying agents.

The route of administration can be percutaneous, via mucosal administration, or via a parenteral route (intradermal, intramuscular, subcutaneous, intravenous, or intraperitoneal). Vaccine compositions according to the present invention may be administered alone, or can be co-administered or sequentially administered with other treatments or therapies.

The present invention also relates to methods of immunizing or inducing an immune response in non-human animals (e.g., pigs) comprising administering to said animal a polypeptide, nucleic acid, cell, vector or vaccine as described above.

The present invention also relates to methods of treating and/or preventing PCV2 associated diseases in non-human animals (e.g., pigs) comprising administering to said animal a polypeptide, nucleic acid, cell, vector or vaccine as described above.

As mentioned above, PCV2 infections or associated diseases include inter alia Postweaning Multisystemic Wasting Syndrome (PMWS), Porcine Dermatitis and Nephropathy Syndrome (PDNS), Porcine Respiratory Disease Complex (PRDC), reproductive disorders, granulomatous enteritis, exudative epidermitis, necrotizing lymphadenitis, and congenital tremors.

The vaccine of the invention can conveniently be administered intranasally, transdermally (i.e., applied on or at the skin surface for systemic absorption), parenterally, ocularly, etc. The parenteral route of administration includes, but is not limited to, intramuscular, intravenous, and intraperitoneal routes and the like.

The dosage of the vaccines of the present invention will depend on the species, breed, age, size, vaccination history, and health status of the animal to be vaccinated, as well as the route of administration, e.g., subcutaneous, intradermal, oral intramuscular or intravenous administration.

The vaccines of the invention can be administered as single doses or in repeated doses. The vaccines of the invention can be administered alone, or can be administered simultaneously or sequentially administered with one or more further compositions, such as other porcine immunogenic or vaccine compositions. Where the compositions are administered at different times, the administrations may be separate from one another or overlapping in time.

In one embodiment, the vaccine compositions of the invention are administered to a subject susceptible to or otherwise at risk for PCV2 infection to enhance the subject own immune response capabilities. The subject to which the vaccine is administered is in one embodiment a pig. The animal may be susceptible to infection by PCV2 or a closely related virus.

Vaccines of the invention are preferably administered to pigs, adult pigs, and also young pigs, piglets or pregnant females, or to other types of non human animals. Vaccination of pregnant females is particularly advantageous as it confers passive immunity to the newborns via the transmission of maternal antibodies. The pigs may be less than 7, 6, 5, 4, 3, 2 or 1 week old; 1 to 6 weeks old; 2 to 5 weeks old; or 3 to 4 weeks old. For instance, "test" animals may be administered the vaccine of the invention in order to evaluate the performance of the vaccine with a view to eventual use or development of a vaccine for pigs. Desirably, the vaccine is administered to a subject who has not yet been exposed to a PCV2 virus. Preferably, the subject is a pig which is in need of vaccination against Postweaning Multisystemic Wasting Syndrome (PMWS) and/or Porcine Dermatitis and Nephropathy Syndrome (PDNS).

The present invention also includes a combination vaccine, comprising vaccines of the invention and at least one immunogenic active component effective against another disease-causing organism in swine such as *Actinobacillus pleuropneunomia*; Adenovirus; *Balantidium coli*; *Bordetella bronchiseptica*; *Brachyspira* spp., preferably *B. hyodyentheriae* and *B. pilosicoli, Brucella suis*, preferably biovars 1, 2 and 3; Classical swine fever virus, African swine fever virus; *Chlamydia* and *Chlamydophila* spp., preferably *C. pecorum* and *C. abortus; Clostridium* spp., preferably *Cl. difficile* and *Cl. perfringens*; Porcine Respiratory Coronavirus; *Cryptosporidium parvum; Eimeria* spp.; *Eperythrozoonis suis* currently named *Mycoplasma* haemosuis; *Erysipelothrix rhusiopathiae; Escherichia coli; Haemophilus* parasuis; Hemagglutinating encephalomyelitis virus; *Isospora suis; Lawsonia intracellulars; Leptospira* spp., preferably *Leptospira Pomona; Mannheimia haemolytica; Mycobacterium* spp., preferably *M. avium; Mycoplasma hyponeumoniae; Pasteurella multocida*; Porcine cytomegolovirus; Porcine parovirus; Porcine reproductive and respiratory syndrome virus; Pseudorabies virus; Rotavirus; *Salmonella* spp., preferably *S. thyhimurium* and *S. choleraesuis; Staphylococcus* spp., preferably *S. hyicus; Streptococcus* spp., preferably *S. suis*; Porcine Cytomegalovirus; Swine influenza virus; Swinepox virus; *Toxoplasma gondii*; Vesicular stomatitis virus and the virus of vesicular exanthema of swine; or other isolates and subtypes of porcine circovirus.

The present invention also provides a container comprising an immunologically effective amount of a polypeptide, nucleic acid or vaccine as described above. The invention also provides vaccination kits comprising an optionally sterile container comprising an immunologically effective amount of the vaccine, means for administering the vaccine to animals, and optionally an instruction manual including information for the administration of the immunologically effective amount of the composition for treating and/or preventing PCV2 associated diseases.

Further aspects and advantages of the invention are provided in the following section, which should be considered as illustrative only.

EXAMPLES

Example 1: Construction of a Nucleic Acid Encoding an Antigenic Polypeptide Comprising the B5R Signal Peptide and PCV2 ORF2

Two synthetic double-strand DNAs shown in SEQ IDs NO: 6 and NO: 7 were ordered from Takara Bio (Japan). Their 5'/3' terminal restriction enzyme sites are BamHI/SalI and XbaI/SalI, respectively. The DNAs were cloned into plasmids, pMD18-Ess (B/X/S) and pMD18-ORF2(X/S), respectively.

As there is XbaI site in the front of 3'-terminal SalI site of SEQ ID NO: 6, the pMD18-Ess (B/X/S) was cut with two restriction enzymes, XbaI and SalI. The DNA fragments of 561 bp which were derived from pMD18-ORF2(X/S) cut with XbaI and SalI were inserted into the XbaI/SalI site of pMD18-Ess (B/X/S). The resulting plasmid, pMD18-Ess_ORF2, includes the antigenic peptide gene of SEQ ID NO: 5.

The plasmid, pGTPs40K-S (described in FIG. 2 of U.S. Pat. No. 7,348,422) was cut with two restriction enzymes, BamHI and SalI, and replaced with a BamHI/SalI cut-0.7 kbp fragment derived from pMD18-Ess_ORF2. The resulted plasmid was named as pGTPs-Ess_ORF2. This plasmid includes a strong poxvirus promoter (Ps) and the antigenic peptide gene of SEQ ID NO: 5.

Example 2: Plasmids for Making Recombinant SPV

Firstly, the SPV genomic DNA was prepared as follows:
SPV kasza strain (VR-363) and embryonic swine kidney cell, ESK-4 cells (CL-184) could be purchased from the American Type Culture Collection (ATCC). The ESK-4 cells were routinely cultured at 37° C. in 5% $CO_2$ in Ham's F-12K medium (Gibco, Cat. No.: 21127-022) supplemented with 1% streptomycin-penicillin (Gibco, Cat. No.: 15140-122) and 5% FBS (Gibco, Cat. No.: 10437-028). For SPV genomic DNA preparation, confluent ESK-4 cells in a 225 $cm^2$ flask were infected with SPV and incubated for 6 days until the cells were showing 100% cytopathic effect (CPE). The infected cells were then harvested by scraping the cells into the medium and centrifuging at 1300 rpm for 5 min. The medium was decanted, and the cell pellet was gently resuspended in 2 ml Phosphate Buffered Saline (PBS: 1.5 g $Na_2HPO_4$, 0.2 g $KH_2PO_4$, 0.8 g NaCl and 0.2 g KCl per litter $H_2O$) and subjected to two successive freeze-thaws. Cellular debris was then removed by centrifuging at 3000 rpm for 5 min at 4° C. SPV virions, present in supernatant, were then pelleted by centrifugation at 20,000×g for 20 min at 4° C. The resultant pellet was then suspended with 10 mM Tris pH7.5. SPV genomic DNAs were then extracted from the SPV virions by suspending with the lysis buffer (20 mM Tris, pH9, 0.1M $NaCl_2$, 5 mM EDTA, 0.1% SDS, 0.2 mg/ml proteinase K) and incubating at 60° C. for 5 min. Phenol: chlororoform (1:1) extraction was conducted two times, and the sample precipitated by the addition of two volumes of ethanol and centrifugation. The supernatant was decanted, and the pellet (SPV DNA) was air dried and rehydrated in 10 mM Tris pH7.5, 1 mM EDTA at 4° C.

Next, the TK flanking regions in the SPV genome were cloned by Polymerase Chain Reaction (PCR). Two primers (synthetic oligonucleotides), SP54242F and SP57617R shown in SEQ ID NOs: 8 and 9 were purchased from Takara Bio. PCR reaction was conducted using LA Taq polymerase (Takara Bio) and a primer set of SP54242F and SP57617R with SPV DNA as a template according to the producer's protocol.

Figure 1:
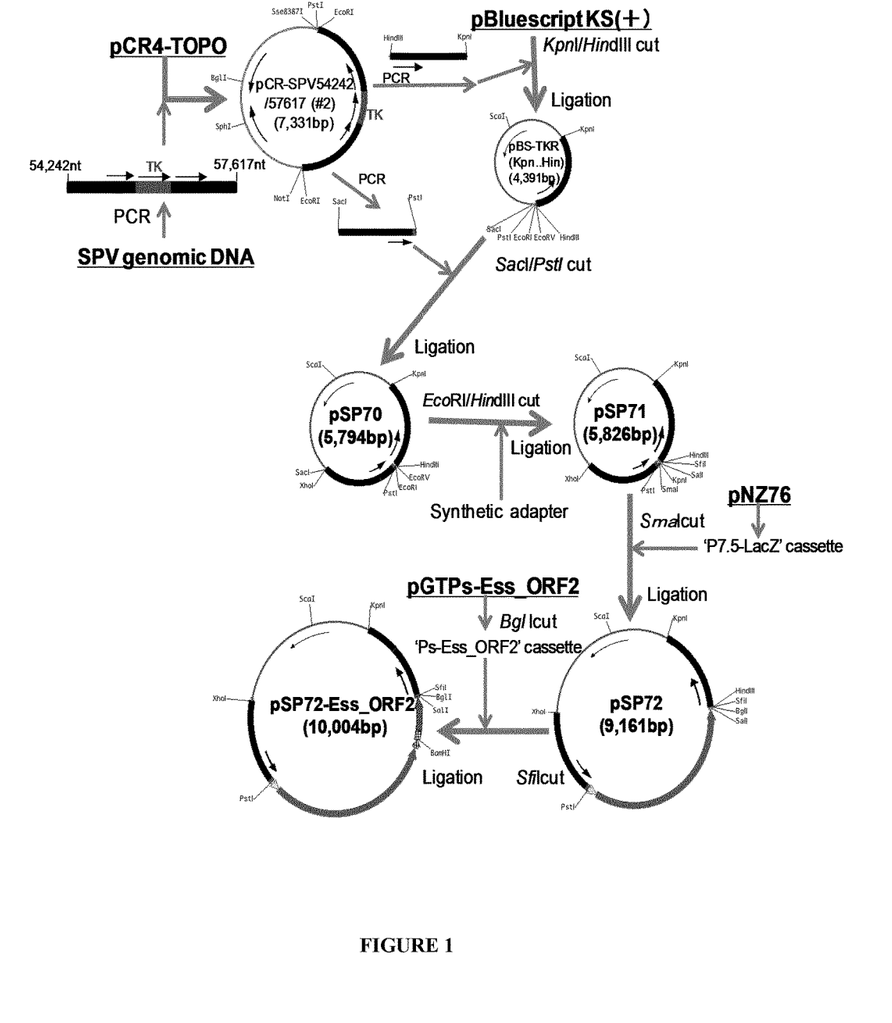
FIG. 1: Construction scheme of the homologous plasmid, pSP72-Ess_ORF2.

The amplified DNA of about 3.4 kbp was confirmed by a 0.8% agarose gel electrophoresis, and purified from the gel using the QIAquick Gel Extraction Kit (Qiagen). The purified DNA fragment was cloned into pCR4-TOPO vector (Invitrogen) according to the producer's protocol. 14 white ampicillin-resistant transformants were picked up and grown in LB broth and each plasmid was prepared with QuickLyse Miniprep Kit (Qiagen). Each plasmid was digested with SpeI, and two kinds of candidate plasmids (both directions of inserted DNA) were selected. The inserted DNAs of them were sequenced with Dye Terminator Cycle Sequencing reagent (DTCS) and CEQ2000XL sequencer (Beckman Coulter). One of the candidate plasmids, pCR-SPV54242/57617 (#2), was confirmed that it contained the DNA fragment from 54,242 nt to 57,617 nt of SPV genomic DNA (GeneBank Acc: NC_003389) and used as a basic plasmid (FIG. 1).

Next, PCR mutagenesis was conducted to delete a part of the TK gene and to introduce the multiple restriction enzyme sites using pCR-SPV54242/57617 (#2) as a template and using two kinds of primer sets, (1) SEQ ID NOs: 10 and 11 or (2) SEQ ID NOs: 12 and 13.

Each PCR products were applied to a 0.8% agarose gel electrophoresis and purified using the QIAquick Gel Extraction Kit. The purified DNA fragment, which was amplified by PCR using a primer set of SEQ ID NOs: 10 and 11, was digested with two restriction enzymes, KpnI and HindIII, and ligated with the same restriction enzymes-cut-pBluescript KS (+) (Stratagene). The resulting plasmid pBS-TKR (Kpn.Hin) (FIG. 1) was digested with SacI and PstI, and the same restriction enzyme-cut DNA fragment, amplified by PCR using a primer set of SEQ ID NOs: 12 and 13, was inserted into it. The resulting plasmid was named pSP70 (FIG. 1).

Between EcoRI and HindIII sites in the multi-restriction enzyme sites of pSP70 were replaced with the oligonucleotide adapter prepared by annealing two synthetic DNA oligonucleotides of SEQ ID NOs: 14 and 15. The resulting plasmid was named pSP71 (FIG. 1).

The DNA fragment of 'P7.5 promoter -LacZ' gene cassette derived from pNZ76, which was cut with HindIII and SmaI of pNZ76 and followed by blunting by DNA polymerase (described in the U.S. Pat. No. 5,387,519) was ligated into SmaI site of pSP71. The resulting plasmid was named pSP72 (FIG. 1), and 'P7.5-LacZ' gene cassette was inserted into the TK gene (from 55625 nt to 56170 nt in the SPV genome).

The 0.8 kb BglI-cut fragment derived from pGTPs-Ess_ORF2 (Example 1) was inserted into SfiI site of pSP72, and the resulting plasmid was named pSP72-Ess_ORF2 (FIG. 1). This plasmid included the 'strong pox virus promoter (Ps)-Ess_ORF2' gene cassette also within the TK gene, and was used as a homology plasmid to make a recombinant SPV, SVR7.

Instead of Ess_ORF2, a natural PCV2-ORF2 gene was inserted into another homology plasmid to use as a reference. Although many sequence data of PCV2-ORF2 were reported, one of them, double-strand DNA of SEQ ID NO: 16, was synthesized. SEQ ID NO: 16 is complement DNA encoding ORF2 of PCV2 isolated from France (GenBank: AF055393), and BamHI and SalI sites are attached at the 5' and 3' ends of it, respectively. The synthesized DNA was cut with BamHI and SalI and replaced with the BamHI/SalI region of pSP72-Ess_ORF2. The resulting plasmid was named pSP72-ORF2 and used as a homology plasmid to make a recombinant SPV, SVR3.

Example 3: Production of Recombinant SPVs, SVR3 and SVR7

(1) Producing Recombinant SPVs, SVR3 and SVR7
Recombinant SPVs were generated in ESK-4 cells by homologous recombination between wild-type SPV genome and homology vectors. Sub-confluent ESK-4 cells in a 6-well plate were infected with wild-type SPV, 4 h prior to transfection with each 2 μg of pSP72-Ess_ORF2 or pSP72-ORF2 using Lipofectamin Plus reagent (Invitrogen) and allowed to incubate at 37° C. for 5 days until cytopathic effect (CPE) had occurred. Cell lysates from infected-transfected cells were screened for recombinant plaques expressing β-galactosidase by the addition of 0.5 mg/ml Bluo-gal (Invitrogen Cat. No.: 15519-028) in the nutrient agarose overlay. Wild-free recombinant viruses were purified through 4-6 rounds of screening. Recombinant SPVs produced using pSP72-Ess_ORF2 or pSP72-ORF2 were named SVR7 and SVR3, respectively.

(2) Black Plaque Assay (BPA)

Figure 2:
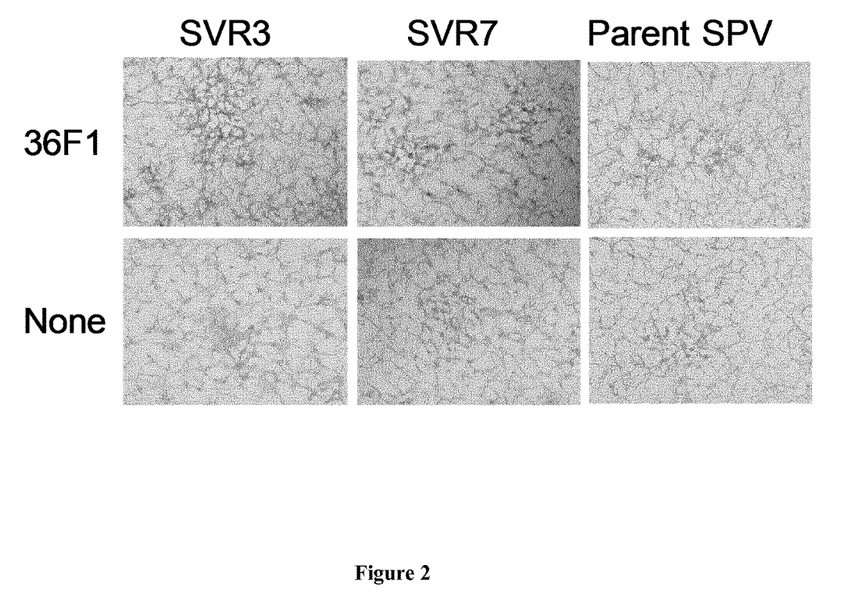
FIG. 2: Black plaque assay of rSPV (SVR3, SVR7) using Monoclonal antibody 36F1. ESK-4 cells were infected with parent SPV or recombinants (SVR3 or SVR7). Six days later, cells were subjected to black plaque assay using Monoclonal antibody 36F1 (1:500), biotin conjugated rabbit anti-Mouse IgG, and ABC-ALP (Vectastain).
Figure 3:
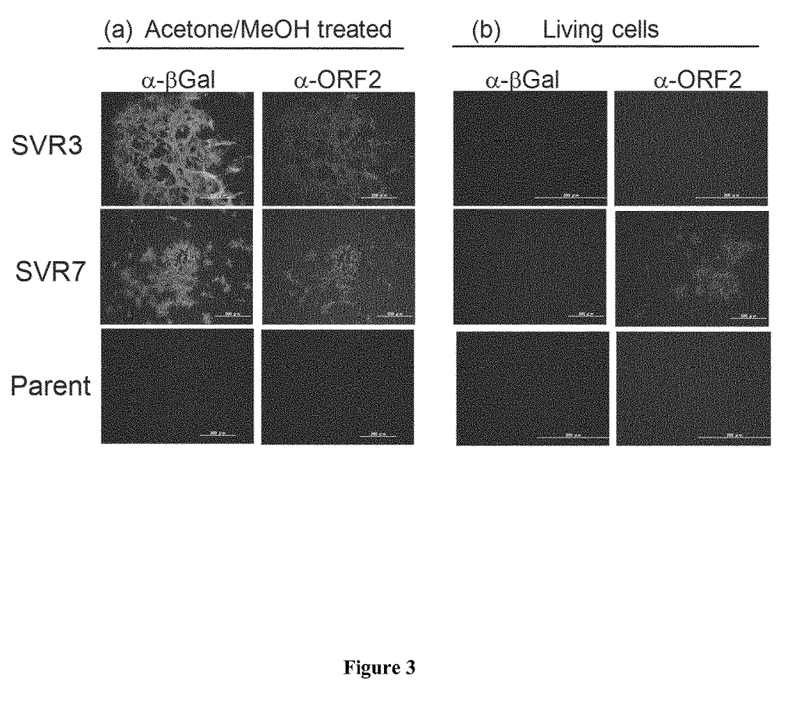

ESK-4 cells in a 24-well plate were infected with SVR3, SVR7 or wild SPV, and incubated at 37° C. After 6 days, the monolayer was fixed with acetone and methanol (2:1). The neutralizing anti-PCV2 monoclonal antibody (Ingenase clone 36F1) was diluted (1:500 dilution) in 5% dried milk in PBS and applied to the infected cells and incubated for 2 h at room temperature (RT). The infected cells were washed with PBS and reacted with biotin conjugated rabbit anti-Mouse IgG (1:1000 dilution), and VECTASTAIN ABC Standard Kit (Vector Laboratory PK-4000). Alkaline phosphatase substrate, NBT/BCIP stock solution (Roche, Cat. No.: 11681451001), was diluted in 0.1M Tris pH 9.5, 0.1M NaCl, 50 mM $MgCl_2$, and added to the infected cells and incubated for 5-30 min at RT until plaques of SVR3 or SVR7 turned a purple/black color. Whereas plaques by wild SPV were white (negative), all plaques by SVR3 and SVR7 were confirmed to be black (positive) (FIG. 2).

Example 4: Polyclonal Antibodies to Detect PCV2-ORF2

To make polyclonal antibody against PCV2-ORF2, the Glutathione S-transferase (GST) fusion proteins with C-terminus region of PCV2-ORF2 were expressed in E. coli. Firstly, a DNA fragment was produced by PCR using pMD18-ORF2(X/S) (Example 1) as a template and a primer set of SEQ ID NOs: 17 and 18.

The amplified DNA of 0.45 kbp was cut with BamHI and SalI, and inserted into BamHI/SalI sites of pGEX-6p-3 (GE Healthcare, 28-9546-51). Candidate plasmids were sequenced with sequencing primers, pGEX-5'-SP or -3'-SP (GE Healthcare, 27-1410-01 or 27-1411-01, respectively) and confirmed to be the same as the construction plan. The resulting plasmid was named pGEX-TGXR2.

*E. coli* host cells, BL21 (GE Healthcare, 27-1542-01) were transformed with pGEX-TGXR2, and transformants were confirmed to express the fusion protein of about 40 kDa by Isopropyl β-D-thio-galactoside (IPTG) induction.

To produce the fusion protein for animal immunization, a single colony of the transformant was inoculated into 5 ml aliquots of LB broth containing 50 μg/ml ampicillin (Amp), and cultivated overnight at 37° C. with shaking. Next morning, overnight culture was inoculated into 1 liter of LB broth containing Amp, and cultivated at 37° C. with shaking to an $OD_{600}$ of 0.7, when IPTG was added into the cultures to a final concentration of 0.1 mM. Cultures were incubated for an additional 3 hrs at 37° C. with shaking. Bacteria were collected by centrifugation at 3500×g for 20 min, and resuspended in 20 ml of PBS lysis buffer (1% Triton X-100 in PBS). Bacterial suspension was sonicated on ice in 10 sec bursts with 10 sec of resting on ice three times. The lysate was centrifuged at 17,000×g for 20 minutes at 4° C., and the supernatant was transferred to a fresh tube.

As the objective GST-fusion proteins were formed inclusion bodies, they were purified with Mini Whole Gel Eluter (Bio-Rad Laboratories, Cat. No.: 165-1255) according to provider's instructions.

The objective GST fusion proteins of ~40 kDa were purified in the fraction No. 7 from Mini Whole Gel Eluter (FIG. 3*b*). Solution of the fraction No. 7 was dialyzed with PBS.

Polyclonal antibodies against this fusion protein were produced by immunizing rats. Three Wister female rats (SPF) at the age of 5 weeks were immunized subcutaneously with 0.1 mg of the GST-ORF2 protein as emulsions in complete Freund's adjuvant, and three weeks later, they were boosted with 0.05 mg of the same antigen mixed with incomplete Freund's adjuvant three times at 3-week intervals. Two weeks later after the last immunization, rats were exanguinated to collect serum of ~1 ml per rat.

Example 5: Characterization of Antigenic Peptides Expressed by Recombinant SPVs Immunofluorescence assay (IFA) was conducted to confirm the localization of the ORF2 proteins expressed by SVR3 or SVR7. ESK-4 cells were infected with rSPV (SVR3 or SVR7) or parental SPV. Five days later, infected cells were washed with PBS twice, treated at room temp for 5 minutes with (a) acetone/methanol (2:1) or (b) PBS. Acetone/methanol or PBS was taken off, and PBS was added not to let the specimens dry out. They were washed twice with PBS and reacted at 37° C. for 30 min with primary antibodies [Rabbit anti-β-Galactosidase (α-βGal) (CAPPEL, Cat.#: 0631-0002) and Rat anti-PCV2-ORF2 (α-ORF2) (Example 4), (1:1000 dilutions in PBS)]. Next, specimens were washed with PBS three times, and reacted at 37° C. for 30 min with secondary antibodies [Goat anti-rabbit IgG (H+L) Alexa Fluor 488 (Life technology, A-11006) and anti-Rat IgG (H+L) Alexa Fluor 546 (A-11081) (1:1,000 dilutions in PBS)]. Specimens were washed with PBS three times, and observed in a fluorescence microscope.

In the case of (a) Acetone/MeOH treated cells, both β-galactosidase (green signal) and ORF2 (red signal) were observed in the cells infected with each of SVR3 or SVR7, because cell membranes were permeable (FIG. 3*a*). On the contrary, in the case of (b) intact cells, both β-galactosidase (green) and ORF2 (red) were not detected on cells infected with SVR3, but ORF2 (red) were clearly observed on cells infected with SVR7 (FIG. 3*b*). These results strongly indicated that localization of ORF2 proteins changed from intracellular such as original ORF2 expressed by SVR3 to extracellular and on the cell surfaces by SVR7.

Therefore, vaccine efficacy by SVR7 is stronger than SVR3, and B5R-derived addressing signal could improve immune response against PCV2-ORF2.

Example 6: In Vivo Vaccination Efficacy

Pigs were vaccinated with vectors encoding a polypeptide of the invention SVR7. As a comparative example, pigs were vaccinated with SVR3. For immunization, 3-5×$10^4$ $TCID_{50}$/dose were injected. The pigs were then challenged with PCV2.

More specifically, 24 piglets, that are PCV2-free or negative, were installed at 3 weeks of age, before vaccination and broken down into distinct groups as represented below:

Group SVR3: 7 piglets, ♂4, ♀3.
Group SVR7: 7 piglets, ♂4, ♀3.
Group Non-Immunized: 7 piglets, ♂4, ♀3.
Group Non-Immunized, non-challenged: 3 piglets, ♂3.

Vaccination was performed at 4 weeks of age and the PCV2 challenge was conducted 2 weeks after immunization. For PCV2 challenge, 6×$10^5$ $TCID_{50}$ of PCV2/dose were injected. At necropsy (4 weeks after PCV2 challenge), several organs were collected for PCV2 detection, including tree lymphoid organs, tonsil, inguinal lymph nodes, intestinal lymphoids and thymus.

PCV2 genome copy number was determined in the serum 1, 2 and 3 weeks post vaccination. The results presented below show that vaccines of the invention induced a strong reduction in PCV2 genome copy number. The results show that the vaccine of the invention is more potent than a vaccine based on a native ORF2 sequence.

TABLE

Percentage (positive/total pigs) of PCV2-qPCR positive pigs in serum

| Group | Pre-immune | Pre-challenge (6 W) | 1 wpc (7 W) | 2 wpc (8 W) | 3 wpc (9 W) |
|---|---|---|---|---|---|
| SVR3 | 0% (0/7) | 0% (0/7) | 17% (1/6) | 33% (2/6) | 100% (6/6) |
| SVR7 | 0% (0/7) | 0% (0/7) | 0% (0/6) | 0% (0/6) | 67% (4/6) |
| NI challenge | 0% (0/7) | 0% (0/7) | 0% (0/7) | 29% (2/7) | 100% (7/7) |
| NINC | 0% (0/3) | 0% (0/3) | 0% (0/3) | 0% (0/7) | 0% (0/3) |

Figure 4:
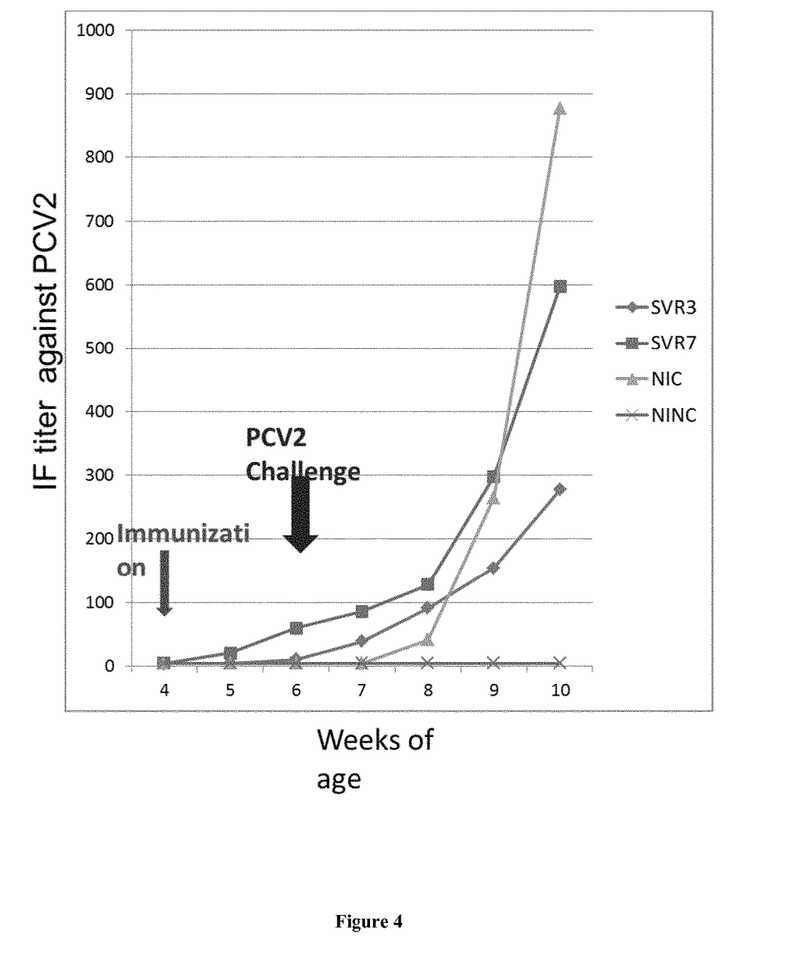

In addition, the results shown in FIG. 4 clearly demonstrate that SVR7 induced a strong anti-PCV2 antibody response. The results show that SVR7 induced substantial antibody to PCV2 ORF2. Antibody response was stronger than with SVR3. The induction of a substantial antibody response correlates with a substantially reduced copy number of PCV2 genome.

These data clearly illustrate the vaccination efficiency of polypeptides and vectors of the invention.

LIST OF SEQUENCES

SEQ ID NO: 1:
KTISVVTLLCVLPAVVYSTCTV

SEQ ID NO: 2:
KTISVVTLLCVLPAVVYSTCTVPTMNNAKLTSTETS

SEQ ID NO: 3:
GVLNTRLSRTFGYTIKRTTVKTPSWAVDMMRFNINDFVPPGGGSNPRSV
PFEYYRIRKVKVEFWPCSPITQGDRGVGSTAVILDDNFVTKATALTYDP
YVNYSSRHTITQPFSYHSRYFTPKPVLDSTIDYFQPNNKRNQLWLRLQT
AGNVDHVGLGTAFENSKYDQEYNIRVTMYVQFREFNLKDPPLNP

SEQ ID NO: 4:
KTISVVTLLCVLPAVVYSTCTVPTMNNAKLTSTETSWKKEKGVLNTRLS
RTFGYTIKRTTVKTPSWAVDMMRFNINDFVPPGGGSNPRSVPFEYYRIR
KVKVEFWPCSPITQGDRGVGSTAVILDDNFVTKATALTYDPYVNYSSRH
TITQPFSYHSRYFTPKPVLDSTIDYFQPNNKRNQLWLRLQTAGNVDHVG
LGTAFENSKYDQEYNIRVTMYVQFREFNLKDPPLNP

SEQ ID NO: 5:
ATGAAAACGATTTCCGTTGTTACGTTGTTATGCGTACTACCTGCTGTTG
TTTATTCAACATGTACTGTACCCACTATGAATAACGCTAAATTGACGTC
TACCGAAACATCGTGGAAAAAAGAGAAAGGAGTCTTGAACACCAGATTG
TCTAGAACCTTCGGTTACACCATTAAGAGAACCACCGTCAAAACCCCAT
CTTGGGCTGTCGATATGATGAGATTCAACATCAACGATTTCGTCCCACC
TGGTGGTGGATCAAACCCTAGATCCGTTCCATTCGAGTACTACAGAATC
AGAAAAGTCAAAGTCGAGTTCTGGCCATGCTCTCCTATTACTCAGGGTG
ATAGAGGAGTTGGATCAACTGCCGTCATCTTGGATGACAACTTCGTCAC
TAAGGCTACTGCCTTGACCTACGATCCTTACGTCAATTACTCTAGTAGA
CACACCATCACCCAACCATTCTCATACCATTCCAGATACTTCACTCCAA
AACCTGTCTTGGACTCAACCATCGATTACTTTCAACCAAACAACAAGAG
AAACCAATTGTGGTTGAGATTGCAAACTGCCGGTAACGTCGATCATGTC
GGATTGGGAACCGCCTTCGAAAACTCCAAATACGACCAGGAGTACAACA
TTAGAGTCACCATGTACGTCCAATTCAGAGAGTTCAACTTGAAGGACCC
ACCATTGAACCCATAA

SEQ ID NO: 6:
GGATCCACCATGAAAACGATTTCCGTTGTTACGTTGTTATGCGTACTAC
CTGCTGTTGTTTATTCAACATGTACTGTACCCACTATGAATAACGCTAA
ATTGACGTCTACCGAAACATCGTGGAAAAAAGAGAAAGGAGTCTTGAAC
ACCAGATTGTCTAGACATTGAACCCATAAGTCGAC

SEQ ID NO: 7:
TCTAGAACCTTCGGTTACACCATTAAGAGAACCACCGTCAAAACCCCAT
CTTGGGCTGTCGATATGATGAGATTCAACATCAACGATTTCGTCCCACC
TGGTGGTGGATCAAACCCTAGATCCGTTCCATTCGAGTACTACAGAATC
AGAAAAGTCAAAGTCGAGTTCTGGCCATGCTCTCCTATTACTCAGGGTG
ATAGAGGAGTTGGATCAACTGCCGTCATCTTGGATGACAACTTCGTCAC
TAAGGCTACTGCCTTGACCTACGATCCTTACGTCAATTACTCTAGTAGA
CACACCATCACCCAACCATTCTCATACCATTCCAGATACTTCACTCCAA
AACCTGTCTTGGACTCAACCATCGATTACTTTCAACCAAACAACAAGAG
AAACCAATTGTGGTTGAGATTGCAAACTGCCGGTAACGTCGATCATGTC
GGATTGGGAACCGCCTTCGAAAACTCCAAATACGACCAGGAGTACAACA
TTAGAGTCACCATGTACGTCCAATTCAGAGAGTTCAACTTGAAGGACCC
ACCATTGAACCCATAAGTCGAC

SEQ ID NO: 8:
AATATTACGGGTGCTGTTT

SEQ OD NO: 9:
AAAAACATCGTATTCCTG

SEQ ID NO: 10:
CGTTCATGTTAAGCTTAACCTGAAATATTG

SEQ ID NO: 11:
GTTTAAACGAATTCGGTACCCTTAAAAACATCG

SEQ ID NO: 12:
CGCCGAGCTCGAGAATATTACGGGTGCTGTTTTTAC

SEQ ID NO: 13:
CCAGACTGCAGAGAACATAGGTCCTAATATAAG

SEQ ID NO: 14:
AATTGCCCGGGTACCGTCGATCGACTTTTTATGGCCCCCCCGGCCA

SEQ ID NO: 15:
AGCTTGGCCGGGGGGGCCATAAAAAGTCGATCGACGGTACCCGGGC

SEQ ID NO: 16:
GGATCCACCATGACGTATCCAAGGAGGCGTTACCGGAGAAGAAGACACC
GCCCCCGCAGCCATCTTGGCCAGATCCTCCGCCGCCGCCCCTGGCTCGT
CCACCCCCGCCACCGTTACCGCTGGAGAAGGAAAAATGGCATCTTCAAC
ACCCGCCTCTCCCGCACCTTCGGATATACTGTCAAGCGAACCACAGTCA
GAACGCCCTCCTGGGCGGTGGACATGATGAGATTCAATATTAATGACTT
TCTTCCCCCAGGAGGGGGCTCAAACCCCCGCTCTGTGCCCTTTGAATAC
TACAGAATAAGAAAGGTTAAGGTTGAATTCTGGCCCTGCTCCCCGATCA
CCCAGGGTGACAGGGGAGTGGGCTCCAGTGCTGTTATTCTAGATGATAA
CTTTGTAACAAAGGCCACAGCCCTCACCTATGACCCCTATGTAAACTAC
TCCTCCCGCCATACCATAACCCAGCCCTTCTCCTACCACTCCCGCTACT
TTACCCCCAAACCTGTCCTAGATTCCACTATTGATTACTTCCAACCAAA
CAACAAAAGAAACCAGCTGTGGCTGAGACTACAAACTGCTGGAAATGTA
GACCACGTAGGCCTCGGCACTGCGTTCGAAAACAGTATATACGACCAGG
AATACAATATCCGTGTAACCATGTATGTACAATTCAGAGAATTTAATCT
TAAAGACCCCCCACTTAACCCTTAATAGTCGAC

SEQ ID NO: 17:
GGTGGTGGATCCAACCCTAGATCCG

SEQ ID NO: 18:
GGTGGGTCGACCAAGTTGAACTCTCTG

The invention claimed is:

1. A polypeptide comprising a cell-membrane addressing peptide directly operably linked to a heterologous antigenic polypeptide, wherein the cell membrane addressing peptide is located N-terminally, and wherein the sequence of said cell membrane addressing peptide is 50 amino acids or less in length and contains SEQ ID NO: 1 or a sequence having at least 90% identity to SEQ ID NO: 1.

2. The polypeptide of claim 1, wherein the cell membrane addressing peptide consists of: SEQ ID NO: 1; a sequence having at least 90% identity to SEQ ID NO: 1; or SEQ ID NO: 2.

3. The polypeptide of claim 1, wherein the cell membrane addressing peptide comprises SEQ ID NO: 2 and is 50 amino acids or less in length.

4. The polypeptide of claim 1, wherein the antigenic polypeptide is a viral antigenic polypeptide.

5. The polypeptide of claim 4, wherein the antigenic polypeptide is an antigenic polypeptide of a Porcine Circovirus Type 2 (PCV2) virus.

6. The polypeptide of claim 5, wherein the antigenic polypeptide is an ORF2 of a PCV2 virus or an antigenic domain thereof.

7. The polypeptide of claim 6, wherein the antigenic polypeptide comprises the sequence of SEQ ID NO: 3 or a sequence having at least 80% identity to SEQ ID NO: 3.

8. The polypeptide of claim 1, comprising the amino acid sequence of SEQ ID NO: 4.

9. The polypeptide of claim 8, further comprising an N-ter methionine residue.

10. The polypeptide of claim 1, which is glycosylated.

11. A polypeptide comprising a signal peptide directly operably linked to an antigenic polypeptide from a Porcine Circovirus Type 2 (PCV2) virus, wherein the signal peptide is located N-terminally and the antigenic polypeptide is located C-terminally, and wherein the signal peptide consists of SEQ ID NO: 1.

12. A vaccine composition comprising a polypeptide according to claim 1 and a carrier or excipient.

13. The vaccine composition according to claim 12, said vaccine composition further comprising a diluent, adjuvant, freeze drying stabilizer, wetting or emulsifying agent, pH buffering agent, gelling or viscosity enhancing additive, or preservative.

14. A method of inducing an immune response in a non-human animal comprising administering a polypeptide according to claim 1 to said non-human animal.

* * * * *